United States Patent [19]

Jirak

[11] 4,119,103
[45] Oct. 10, 1978

[54] DETACHABLE POWER SOURCE WITH LOW CURRENT LEAKAGE

[75] Inventor: Thomas L. Jirak, Plymouth, Minn.

[73] Assignee: Medtronic, Inc., Minneapolis, Minn.

[21] Appl. No.: 735,866

[22] Filed: Oct. 27, 1976

[51] Int. Cl.² ............................................. A61N 1/36
[52] U.S. Cl. ......................... 128/419 PS; 128/419 PG
[58] Field of Search ......... 128/419 E, 419 P, 419 PG, 128/419 PS, 419 R, 421, 422, 423; 307/95, 240, 246

[56] References Cited

U.S. PATENT DOCUMENTS

| | | | |
|---|---|---|---|
| 3,612,898 | 10/1971 | Doniguian et al. | 307/95 |
| 3,667,477 | 6/1972 | Susset et al. | 128/419 E |
| 3,807,411 | 4/1974 | Harris et al. | 128/419 PG X |
| 3,898,994 | 8/1975 | Kolenik et al. | 128/419 PG |
| 3,953,742 | 4/1976 | Anderson et al. | 307/95 |
| 4,010,759 | 3/1977 | Boer | 128/419 PS X |
| 4,010,760 | 3/1977 | Kraska et al. | 128/419 PS |
| 4,024,875 | 5/1977 | Putzke | 128/419 PS X |

*Primary Examiner*—William E. Kamm
*Attorney, Agent, or Firm*—Joseph F. Breimayer; Harry W. Barron

[57] ABSTRACT

A pulsed energy coupling system for transferring energy from a detachable power source to a pulse generator module of an electromedical device. Periodically energy is transferred through coupling members to an energy storage device in the pulse generator module. Leakage current losses between coupling members at different electrical potentials is minimized by maintaining coupling members at the same potential during the time intervals between energy transfers. Energy transfers are triggered and effected either at independent, fixed intervals or as energy necessary to power the pulse generator module is dissipated from the energy storage device.

20 Claims, 5 Drawing Figures

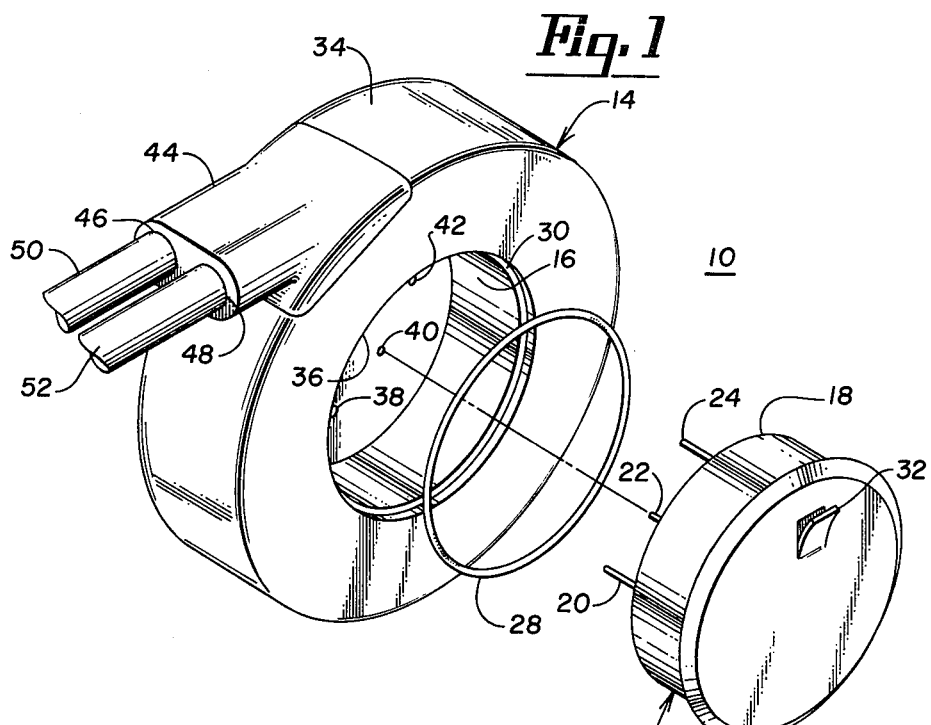
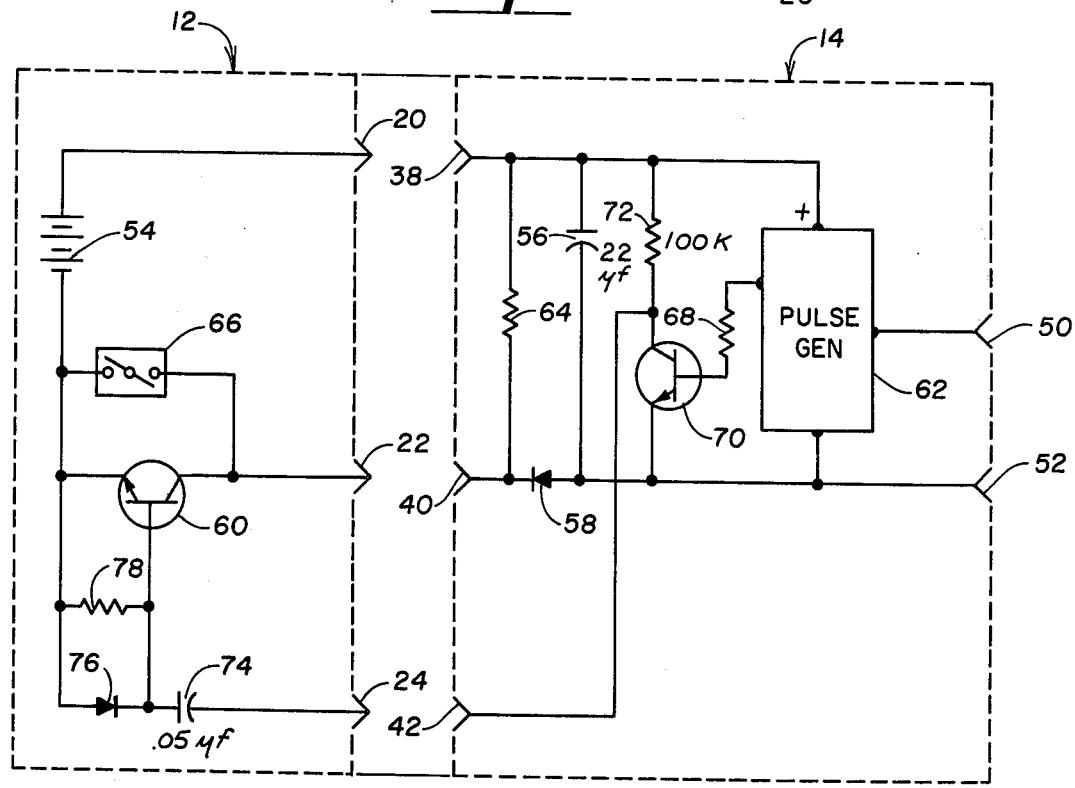

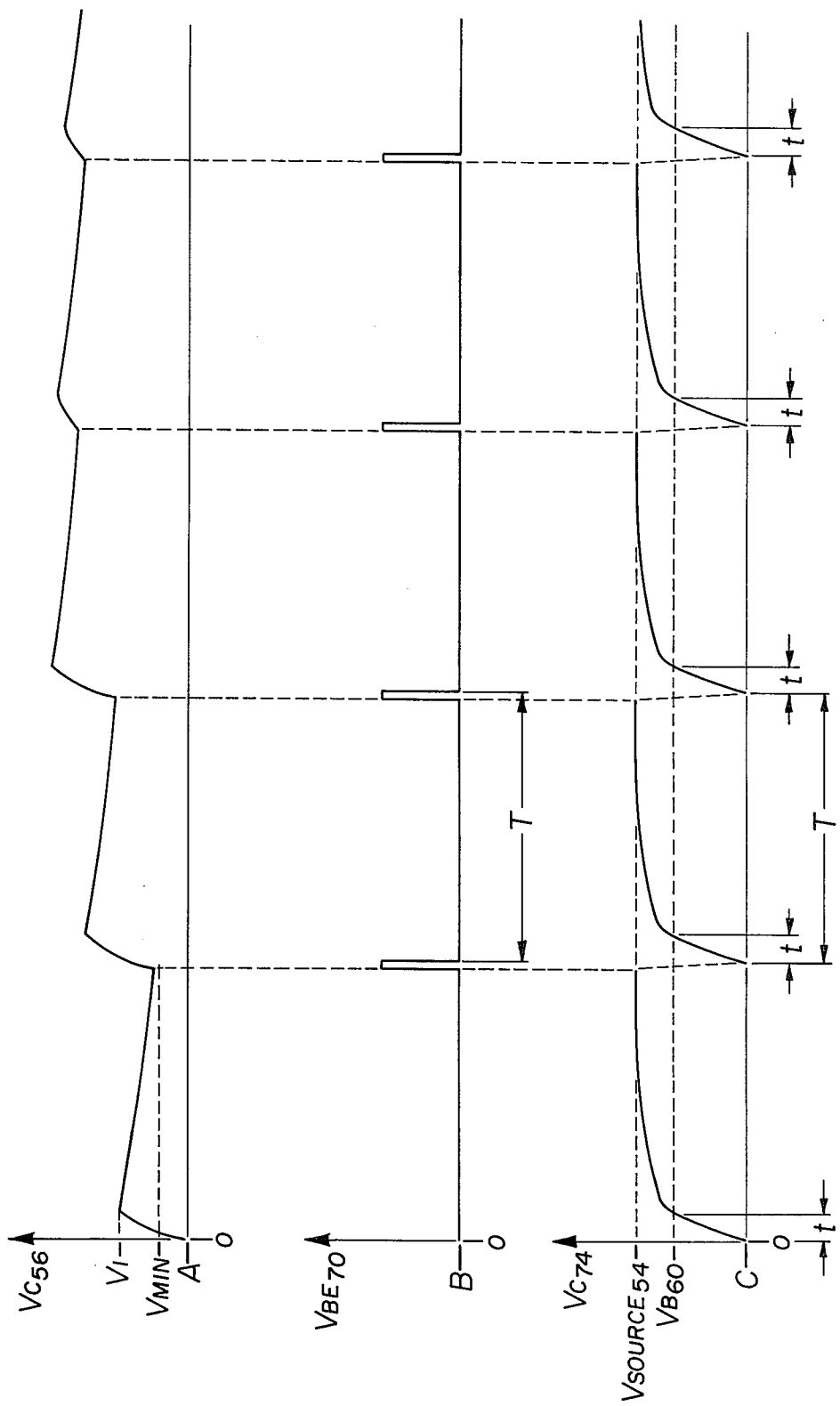

DETACHABLE POWER SOURCE WITH LOW CURRENT LEAKAGE

BACKGROUND OF THE INVENTION

This invention relates to the field of implantable electromedical devices. In particular, it relates to an implantable electromedical device having a replaceable power supply module.

Implantable electromedical devices such as cardiac pacemakers have been known and commercially used for many years. In time, the power supply depletes and the entire pacemaker system, consisting of a power supply module and electronic stimulating signal generating module, is replaced. There are several advantages to be obtained in simply replacing the depleted power supply. One is the cost savings in retaining the original signal generating module. Another is the convenience and minimization of risk which results from not having to disturb the implanted signal generating module and its associated leads connected to the tissue to be stimulated. A third is flexibility in instrumentation afforded by replacing one power supply with another of a different type should the patient's requirements change.

While the general concept of a replaceable power supply for electromedical devices is not new, there is a significant barrier to its adaptation to the field of implantable electromedical devices. This barrier is the result of the hostile environment presented by electrolytic body fluids. These conductive fluids inevitably infiltrate the junction between the power supply and signal generating modules, permitting current leakage from the power supply via the connector pins or other means for electrically joining the two modules. This current leakage substantially reduces the active life of the device as well as corrode the connector pins.

SUMMARY OF THE INVENTION

The present invention overcomes this barrier not by eliminating exposure of the connecting parts of the modules to body fluid but by reducing the time energy is transferred between modules to a fraction of the time the signal generating module would conventionally draw energy during its implanted life. As a consequence, current leakage is proportionally reduced to an acceptable level since leakage only occurs during the time of energy transfer between modules. Corrosion of connecting parts, a function of current leakage, is likewise substantially reduced to an acceptable level. Several embodiments of the invention have been devised, all utilizing internal electronic means to limit energy transfer between the modules to a brief enough time to reduce current leakage substantially, yet sufficient to maintain the energy in the signal generating module at an operating level. In general, the power supply module contains an energy source (such as a battery) and energy transfer means for periodically transferring energy to the signal generating module producing the stimulating signal. Located in either the power supply module or the signal generating module, or both, is electronic circuitry for triggering or activating the energy transfer means to allow sufficient transfer of energy in a short time to maintain the signal generating circuitry at an operating level. The triggering circuitry may be an oscillator which provides for energy transfer at fixed intervals, or a voltage sensing device located in the signal generating module that senses the level of energy in an energy storage device supplying the signal generating circuitry. A preferred embodiment, especially for cardiac pacemakers, is electronic means which activates the electronic switching means in response to generation of a tissue stimulating output signal or in response to an electrical signal received from the tissue to be stimulated, or both.

BRIEF DESCRIPTION OF THE DRAWINGS

In the drawings:

FIG. 1 is a pictorial view of an implantable device of this invention with the power supply and signal generating modules separated to show the coupling mechanism;

FIG. 2 is a circuit diagram showing the various electronic functions of a preferred embodiment of the invention;

FIG. 3 is a composite of plots of three voltage waveforms that occur in the circuit depicted in FIG. 3;

DESCRIPTION OF THE PREFERRED EMBODIMENTS

Figure 4:
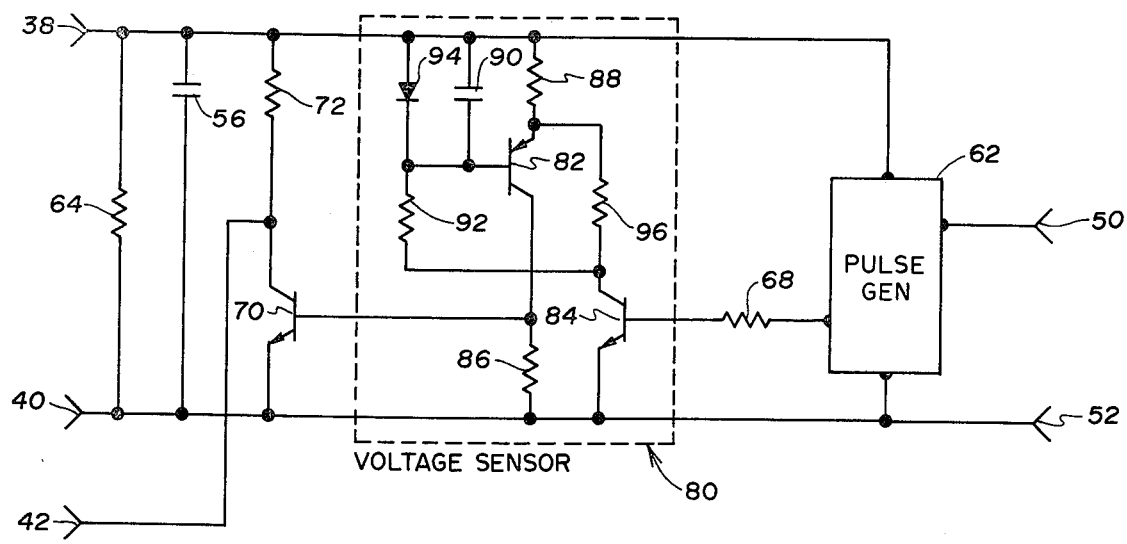
FIG. 4 is a circuit diagram of a second embodiment of the invention.

Referring to FIG. 1, an implantable device 10 of this invention is depicted comprising a power supply module 12 and a signal generating module 14. The module 12 is cylindrically shaped to fit in cavity 16 of module 14. Extending outwardly from surface 18 of module 12 and perpendicular thereto are cylindrically shaped male pins 20, 22, and 24. Pin 20 is connected to the energy source, and pins 22 and 24 are connected to the electronic switch which will be specifically described with respect to FIGS. 2 and 3, hereinafter. Module 12 is provided with a lip 26 and O-ring 28 which fit into a complimentary annular shaped recess 30 in module 14. Located on the opposite surface 19 of module 12 is a tab 32 to facilitate gripping and removal of the module 12 from connection with module 14.

Signal generating module 14 includes housing 34 containing the electronic circuitry for converting the power supplied by module 12 to a suitable stimulating signal as is known in the art. Suitable circuitry includes the circuitry for producing a heart pacemaker pulse, such as the circuitry in the Medtronic ® Model 5950 Implantable Bipolar Demand Pulse Generator. Located in face 36 of cavity 16 are three female receptacles 38, 40 and 42 for receiving male pins 20, 22 and 24. In certain embodiments of the invention, such as that depicted in FIG. 5, for example, only two connector pins and receptacles, or their equivalent are needed. Housing 34 also includes a boot 44 providing a pair of apertures 46 and 48 for receiving conventional electrical leads 50 and 52, respectively.

In FIG. 2, there is shown, partly in block form, the electronic circuitry of a preferred embodiment of the invention. Inside the power source module 12 is the electrical energy source 54 which may consist of mercury, lithium, silver, nuclear or other power source. A typical mercury power source, used in the preferred embodiment, provides an output voltage of 5.4 volts. This electrical energy source supplies the signal generating module 14 with energy, allowing the normal function of the pacemaker when the power source module 12 is connected to the signal generating module 14. The electrical contacts 20, 22 and 24 on module 12 mate with the corresponding contacts 38, 40 and 42, respectively, on the signal generating module 14.

Upon connection of the power source module 12 to the signal generating module 14, one terminal of electrical energy source 54 is connected by mated pins and receptacles, or contacts, 20/38 to one terminal of the energy storage device, or capacitor, 56. The other terminal of the capacitor 56 is connected via diode 58 and mated contacts 22/40 to the electronic switch, or transistor, 60. Energy, or current, from the electrical energy source 54 may transfer through diode 58 to charge capacitor 56 when transistor 60 is conductive. The initial energy transfer is enough to bring the charge on capacitor 56 to a level necessary for the pulse generator circuitry 62, connected in parallel with capacitor 56, to operate normally. After a predetermined time, the electronic switch 60 is rendered nonconductive and current is no longer supplied to the energy storage device 56. By limiting the power delivery duty ratio to less than 20% preferably 10% or less, the amount of leakage current and corrosion that would otherwise occur at the contacts is correspondingly limited. (Duty ratio is equal to 100% times the duration of power delivery pulses divided by the period of power delivery pulses.) Further limiting of leakage current may be obtained by the optional use of leakage current limiting resistor 64 which is connected across contacts 20/38 and 22/40, bringing them both to the same potential as source 54 less the emitter to collector drop in electronic switch transistor 60. The high resistance of resistor 64 limits current loss thereacross.

In addition, the device may be provided with a restart switch 66. At the time of initial operational mating of modules 12 and 14, should electronic switch 60 be opened before the minimum energy to power the pulse generator circuit 62 has been stored in the energy storage device 56, magnetic reed switch 66 can be actuated by an external magnet (not shown). This will provide a bypass circuit directly between the energy source 54 and contacts 22/40 to allow initial transfer of sufficient energy to energy storage device 56.

After the energy storage device 56 is initially charged to a functioning voltage, further energization in the course of operation of the device is accomplished by the triggered transfer of energy from the power source module 12 to the signal generating module 14 at predetermined intervals in accordance with the above defined objects.

Referring again to FIG. 2, when the power supply module 12 is connected to the signal generating module 14, and upon closure of switch 66 if necessary, pulse generator circuit 62 will be energized and capable of producing output pulses across terminals 50 and 52.

It is characteristic of demand pulse generators, such as circuit 62, that an output pulse will be produced across terminals 50 and 52 only if the patient's heart is not beating at an acceptable rate. Since some patients' hearts may beat at acceptable rates for several hours or several days, the output signal at terminals 50 and 52 cannot be relied upon to drive an energy transfer system. However, certain signals are available in typical demand pulse generators that occur each time the patient's heart beats, whether the beat is spontaneous or in response to an output pulse. For example, the pulse interval timing capacitor in the Medtronic ® 5950 demand pulse generator is reset by the output signal of the pulse generator oscillator each time a pace pulse is generated and is also reset by the output signal of the pulse generator sense amplifier each time the patient's heart beats naturally. These output signals from pulse generator 62 are in FIG. 2 applied to the base of transistor 70 via resistor 68. Since the output and signal of the sense amplifier portion of pulse generator 62 occurs each time the patient's heart beats, there is no danger of capacitor 56 losing its charge during a long period of spontaneous cardiac activity. The collector of switching transistor 70 is connected by resistor 72 and contacts 20/38 to power source 54. Resistor 72 (100K ohms) and transistor 70 comprise the elements of an electronic switch trigger respectively, connected by contacts 24/42 and capacitor 74 to the base of transistor 60. Diode 76 and resistor 78 connect the base of transistor 60 to its emitter and to the low potential side of power source 54.

When the power supply module 12 and pulse generator module 14 are mated with capacitor 74 discharge current will flow from the positive terminal of electrical energy source 54 across contacts 20/38 through resistor 72 to mated contacts 24/42. Negligible current will flow into the pulse generator circuit 62 because transistor 60 will be nonconductive at this time. Low capacitance (0.05 microfarad) capacitor 74 will, however, begin charging by the current passing through resistor 72. The anode of the diode 76 is connected to resistor 78, the emitter of transistor 60, and the negative terminal of the electrical energy source 54. The capacitor 74 charging current will be blocked by diode 76 and flow through resistor 78 as well as into the base of transistor 60. Resistor 78 is chosen so that it is very large in value (10 ohms) compared to the input impedance of transistor 60. Therefore, most of the capacitor charging current will return to the negative terminal of the electrical energy source 54 through the base of transistor 60. When enough current flows into the base of transistor 60 it will turn on and conduct current between its collector and emitter terminals. Since the collector of transistor 60 is connected to mated contacts 22/40, these contacts will be effectively short circuited to the negative terminal of the electrical energy source 54. With transistor 60 turned on, current can pass from the positive terminal of the electrical energy source 54 through contacts 20/38 to high capacity storage device 56 (22 microfarads). The anode of diode 58 is connected to capacitor 56 and the cathode of diode 58 is connected to contacts 22/40. Diode 58 completes the charging current path between capacitor 56 and electrical energy source 54. The capacitor 56 will continue to charge through transistor 60 as long as capacitor 74 continues to charge through resistor 72. But, once capacitor 74 has become fully charged, the base current for transistor 60 will be reduced and it will cease conducting current between its collector and emitter terminals. Therefore, the RC charge time of capacitor 74 will determine the time period of energy transfer from power supply module 12 to signal generating module 14.

After transistor 60 has been rendered nonconductive, or turned off, current no longer passes from the positive terminal of electrical energy source 54 through contacts 20/38 to capacitor 56. Capacitor 56 will now supply energy to the pulse generator circuit 64, and diode 58 now presents a high impedance current path to the negative terminal of power source 54. Leakage current resistor 64 remains connected across contacts 20/38 and 22/40 to ensure that both contacts remain at approximately the same positive potential to reduce leakage current and contact corrosion. Any current leakage resulting from a residual potential difference between the contact 20/38 and 22/40 upon cut-off of transistor 60 will flow through the resistor 64, rather than between the contacts. Diode 58 also presents a high impedance between the positive potential and the output terminal 52.

By choosing transistor 60 with the proper gain and the proper values for capacitor 74 and resistor 72, enough energy is stored on capacitor 56 to power the pulse generator circuit 62 until the next triggered intermodule pulsed energy transfer takes place. If the stimulator signal circuitry 62 is that employed in a cardiac pacemaker of the demand type, a trigger pulse can be derived from either of two events. As hereinbefore described, one event occurs when the demand pacemaker produces a stimulating output pulse and another occurs when a natural heart beat is sensed by the sense amplifier portion of the pulse generator 62 which produces a sense amplifier output pulse. In either case, the output pulse conducted to the base of transistor 70 will turn it on, discharging capacitor 74 through its emitter to collector path and to the low potential terminal of capacitor 56. After transistor 70 turns off, capacitor 74 will have been almost fully discharged, and it can begin to charge again through resistor 72. As described before, this charging current will turn transistor 60 on, and energy will be transferred from the electrical energy source 54 into capacitor 56. Capacitor 56 will continue to charge until capacitor 74 becomes fully charged and transistor 60 turns off.

The ratio of transistor 60 on time to off time can be determined by the values of capacitor 74 and resistor 70. By proper choice of these values, leakage current and corrosion rates at the electrical contacts can easily be reduced five or tenfold.

It is important to note that the system described above may be self-starting on condition that capacitor 74 is completely discharged before the power supply module 12 and signal generating module 14 are mated. If, for some reason capacitor 74 is not completely discharged, transistor 60 would not be turned on. As a precaution, therefore, the normally open magnetic reed switch 66 can be closed by placing a magnet over the implanted device to complete the changing path of capacitor 56.

FIG. 3 is a plot of three voltage waveforms that occur in the device having the electronic circuitry of FIG. 2. The first waveform, plot A, is the voltage waveform over time that exists across the capacitor 56. The second waveform, plot B, is the voltage waveform over a corresponding time period between the base and emitter of transistor 70. The third waveform, plot C, is the waveform over the corresponding time period of the voltage across capacitor 74.

Upon initial mating of modules 12 and 14 at time 0 in FIG. 3, the following current paths exist: (1.) positive terminal of battery 54 to contacts 20/38 to resistor 72 to contacts 24/42 to capacitor 74 to base-emitter junction of transistor 60 to the negative terminal of battery 54; and (2.) positive terminal of battery 54, to contacts 20/38, to capacitor 56 to diode 58, to contacts 22/40, to collector-emitter of transistor 60, and then to the negative terminal of battery 54. The second current path causes capacitor 56 to charge to $V_1$ as shown in plot A, and the voltage on capacitor 56 will, if circuit element values have been chosen properly, remain above a minimum voltage, V min, necessary to operate pulse generator circuit 62 over the period T. Energy will be transferred from the power supply module 12 to module 14 for a time $t$ determined by the time it takes capacitor 74 to charge to $VB_{60}$, approximately the voltage of battery 54, thereby turning transistor 60 off. In other words, T is related to the RC time constant of resistor 72 and capacitor 74.

After initial mating, the pulse generator circuitry will be capable of operation. Two possibilities can then occur either a natural heartbeat is sensed by the pacemaker, or the pacemaker applies a pulse to the heart. In either case, the pulse in plot B is applied to the base of transistor 70 closing the following current path: capacitor 74 to contacts 24/42, to collecto-emitter of transistor 70, to diode 58, to contacts 22/40, to the collector-emitter of transistor 60, and the terminal of battery 54, thereby nearly completely discharging the capacitor 74. This low resistance path causes capacitor 74 to discharge quickly and again allows transistor 64 to conduct and further charge capacitor 56 in the time T. Capacitor 82 then successively charges to higher and higher voltage levels depicted in plot A, levels that are well above the minimum operating voltage level V min for pulse generator circuit 62. The time between waveforms in plot B is T. The energy transfer across connector pins 20/38 and 22/40 (plot C) occurs for 100 × $t/T$ percent of the time, limiting leakage current to that percent of the time. Preferably, $t$ should be 1/5 or less of T, most preferably 1/10 or less.

In the event that the capacitor 56 is not charged or maintained above V min, it may be necessary to close switch 66 to fully charge capacitor 66 to commence operation of the pulse generator 62.

Although one form of energy transfer circuit is depicted in FIG. 2, it will be recognized that several other means may be devised to effect the energy transfer. Another means for accomplishing predetermined intermodule energy transfer may be circuitry responsive to the amount of energy stored in energy storage device 56, such means causing transfer of energy from module 12 to module 14 only when the energy level to device 56 is reduced to a predetermined level. Such means would sense this reduction and close electronic switch 60 to provide the requisite energy transfer as described above.

FIG. 4 depicts how a voltage sensor circuit 80 may be added to the pulse generator module 14 to modify the pulse generator so that intermodule energy transfer is responsive to the energy level in the energy storage device 56. In this embodiment, transistor 70 does not conduct and discharge capacitor 74 unless the storage capacitor 56 has discharged to some predetermined value. The voltage sensor circuit 80 is inserted between resistor 68 and transistor 70 of the embodiment depicted in FIG. 1. The combined circuit operates in the same manner as the embodiment of FIG. 1 when the modules are initially mated. When pulse generator 62 is operating, either a naturally occurring heartbeat or a pace output pulse will cause an output pulse from pulse generator 62 that will be coupled via resistor 68 to turn-on transistor 84 (just as transistor 70 was turned on in the embodiment of FIG. 1). Transistor 84 will conduct, putting the full capacitor 56 voltage across the voltage divider formed by resistors 88 and 96, as well as bias diode 94 into conduction via resistor 92. If the capacitor 56 voltage is above a predetermined threshold, the voltage divider formed by resistors 88 and 96 will bias the emitter of transistor 82 negative with respect to its base (the voltage at the base of transistor 82 is determined by the forward drop of diode 94, a LED having a typical forward drop of one and one-half volts). If the emitter of transistor 82 is biased negatively with respect to its base, the transistor 82 is said to be cut off and will not deliver a pulse to the base of transistor 70. Consequently, no inter-module energy transfer will take place. If, however, the voltage on capacitor 56 has fallen below the the predetermined threshold, the voltage delivered to the emitter of transistor 82 by the voltage divider action of resistors 88 and 96 will be insufficient to cut off transistor 82. Under these conditions, transistor 82 will conduct, delivering a pulse to the base of transistor 70. Transistor 70 will then trigger an inter-module energy transfer in the same manner as it did in the embodiment shown in FIG. 1. Capacitor 90 in the voltage sensor 80 circuit is used to filter the switching noise pulses generated by transistor 84 and keep them from turning on transistor 82 unless the voltage on capacitor 56 has fallen below the predetermined threshold. Thus, the voltage sensor 80 blocks pulse generator circuit 62 pulses from turning on transistor 70 and triggering inter-module energy transfers unless the voltage of across capacitor 56 has fallen below some predetermined threshold. Once the voltage on capacitor 56 has fallen below the predetermined threshold, voltage sensor 80 passes the trigger pulses until the capacitor 56 voltage has risen above the threshold. Since the voltage sensor circuit is turned on only during each pulse generator 62 energy transfer trigger pulse, it does not consume an appreciable amount of energy. Since energy transfer is not triggered unless it is needed the amount of exposure to corrosion of the coupling pins 38, 40, and 42 is also reduced.

Figure 5:
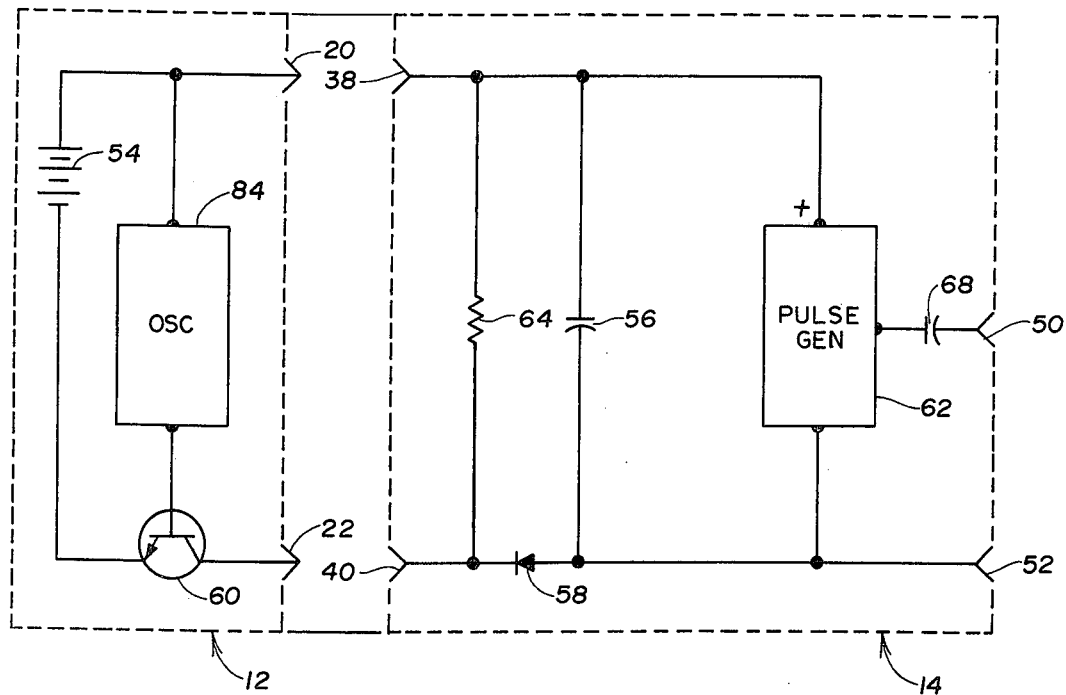
FIG. 5 is a circuit diagram of still another embodiment of the invention.

Referring now to FIG. 5, there is shown a further embodiment of the charge transfer circuitry of the present invention. In this embodiment, an oscillator 85 located in power supply module 12 is provided, eliminating the need for contacts 24/42, the associated circuitry and the restart switch 66 shown in preceeding embodiments. A suitable oscillator 85 may be one of a variety of astable oscillators having a repetition rate of about 75 pulses per minute, and a pulse width of from 50 to 200 milliseconds. Each time the oscillator produces a pulse, the transistor 60 is thereby rendered conductive to close the charge path for capacitor 56 for the pulse width deviation.

The disclosure and description heretofore of three embodiments of the invention has been by way of illustration and not of limitation of the wide scope of the invention and establishes that many other embodiments of the present invention are possible. It is therefore to be understood, that all modifications and variations on the invention occurring to those skilled in the art are intended to be included within the scope of the appended claims.

What is claimed is:

1. A body-implantable electromedical device of the type having electrical energy source means for developing electrical energy, generating means adapted to receive and responsive to electrical energy for periodically generating a tissue stimulating signal, said generating means having output means adapted to be coupled to electrode means for transmitting the stimulating signal to body tissue, coupling means for detachably coupling said electrical energy source means to said generating means, and limiting means for reducing the leakage of electrical energy from said coupling means comprising:
   means for periodically transferring electrical energy from said electrical energy source means to said generating means.

2. The device of claim 1 wherein said transfer means further comprises:
   trigger means for periodically providing a trigger signal; and
   circuit means responsive to the trigger signal for conducting electrical energy through said coupling means.

3. The device of claim 1 wherein said generating means further comprises electrical energy storage means for receiving and storing electrical energy transferred from said electrical energy source means by said transfer means.

4. The device of claim 3 wherein said transfer means further comprises:
   reference potential means for establishing a reference electrical potential;
   comparison means responsive to the reference electrical potential and the electrical potential of the electrical energy stored by said electrical energy storage means for developing a trigger signal when the stored electrical potential falls below the reference electrical potential; and
   circuit means responsive to the trigger signal for conducting electrical energy through said coupling means.

5. The device of claim 2 wherein said circuit means further comprises:
   timing means responsive to the trigger signal for rendering said circuit means conductive for a predetermined duration.

6. The device of claim 2 wherein said trigger means further comprises:
   oscillator circuit means responsive to electrical energy from said electrical energy source means for developing the trigger signal at regular, fixed time intervals.

7. The device of claim 2 wherein said trigger means further comprises means responsive to the generation of a tissue stimulating output signal by said generating means for producing a corresponding trigger signal.

8. The device of claim 2 further comprising sensing means responsive to electrical signals developed by a body organ for producing an output signal for resetting the operation of said generating means for a predetermined time period.

9. The device of claim 8 wherein said trigger means further comprises means responsive to the sense amplifier output pulse for developing a corresponding trigger signal.

10. The device of claim 1 wherein said generating means further comprises electrical energy storage means for receiving and storing electrical energy transferred from said electrical energy source means by said transfer means.

11. A body-implantable electromedical device of the type having electrical energy source means for developing electrical energy, generating means adapted to receive and responsive to electrical energy for generating a tissue stimulating signal, said generating means having output means adapted to be coupled to electrode means for transmitting the stimulating signal to body tissue, at least two coupling means for detachably coupling said electrical energy energy source means to said generating means, and means for reducing the leakage of electrical energy from said coupling means comprising:
means for periodically transferring electrical energy from said electrical energy source means to said generating means; and
means for maintaining the coupling means at the same electrical potential in the time intervals between periodic energy transfers thereby preventing the leakage of electrical energy between said coupling means.

12. The device of claim 11 wherein said transfer means further comprises:
trigger means for periodically providing a trigger signal; and
circuit means response to the trigger signal for conducting electrical energy through said coupling means.

13. The device of claim 11 wherein said generating means further comprises electrical energy storage means for receiving and storing electrical energy transferred from said electrical energy source means by said transfer means.

14. The device of claim 13 wherein said transfer means further comprises:
reference potential means for establishing a reference electrical potential; and
comparison means responsive to the reference electrical potential and the electrical potential of the electrical energy stored by said electrical storage means for developing a trigger signal when the stored electrical potential falls below the reference electrical potential; and
circuit means responsive to the trigger signal for periodically conducting electrical energy through said coupling means.

15. The device of claim 12 wherein said circuit means further comprises:
timing means responsive to the trigger signal for rendering said circuit means conductive for a predetermined duration.

16. The device of claim 12 wherein said trigger means further comprises:
oscillator circuit means responsive to electrical energy from said electrical energy source means for developing the trigger signal at regular, fixed time intervals.

17. The device of claim 12 wherein said trigger means further comprises means responsive to the generation of a tissue stimulating output signal by said generating means for producing a corresponding trigger signal.

18. The device of claim 12 further comprising sensing means responsive to electrical signals developed by a body organ for producing an output signal for resetting the operation of said generating means for a predetermined time period.

19. The device of claim 18 wherein said trigger means further comprises means responsive to the sense amplifier output pulse for developing a corresponding trigger signal.

20. The device of claim 11 wherein said generating means further comprises electrical energy storage means for receiving and storing electrical energy transferred from said electrical energy source means by said transfer means.

* * * * *